United States Patent
Ashworth et al.

(10) Patent No.: US 6,471,723 B1
(45) Date of Patent: Oct. 29, 2002

(54) BIOCOMPATIBLE PROSTHETIC TISSUE

(75) Inventors: Paul Edward Ashworth, Andover, MN (US); Matthew Frank Ogle, St. Paul, MN (US); Daniel Paul McTavish, Fridley, MN (US); Sheila Jeanne Kelly, Vadnais Heights, MN (US); Andrea L. Johnson, Fridley, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/480,437

(22) Filed: Jan. 10, 2000

(51) Int. Cl.[7] .................................................. A61F 2/00
(52) U.S. Cl. ................................... 623/2.42; 623/23.72
(58) Field of Search ............................... 623/2.42, 926, 623/27.72; 435/40.5; 8/94.11, 94.33

(56) References Cited

U.S. PATENT DOCUMENTS

| | | | |
|---|---|---|---|
| 3,988,782 A | 11/1976 | Dardik et al. | 3/1 |
| 4,120,649 A | 10/1978 | Schechter | 8/94.11 |
| 4,323,358 A | 4/1982 | Lentz et al. | 8/94.11 |
| 4,378,224 A | 3/1983 | Nimni et al. | 8/94.11 |
| 4,402,697 A | 9/1983 | Pollock et al. | 8/94.11 |
| 4,405,327 A | 9/1983 | Pollock | 8/94.11 |
| 4,481,009 A | 11/1984 | Nashef | 8/94.11 |
| 4,553,974 A | 11/1985 | Dewanjee | 8/94.11 |
| 4,597,766 A | 7/1986 | Hilal et al. | 623/13 |
| 4,647,283 A | 3/1987 | Carpentier et al. | 623/11 |
| 4,648,881 A | 3/1987 | Carpentier et al. | 623/11 |
| 4,729,139 A | 3/1988 | Nashef | 8/94.11 |
| 4,753,652 A | 6/1988 | Langer et al. | 623/1 |
| 4,770,665 A | 9/1988 | Nashef | 8/94.11 |
| 4,786,287 A | 11/1988 | Nashef et al. | 8/94.21 |
| 4,838,888 A | 6/1989 | Nashef | 623/2 |
| 4,885,005 A | 12/1989 | Nashef et al. | 8/94.11 |
| 4,976,733 A | 12/1990 | Girardot | 623/11 |
| 5,002,566 A | 3/1991 | Carpentier et al. | 623/2 |
| 5,094,661 A | 3/1992 | Levy et al. | 8/94.11 |

(List continued on next page.)

FOREIGN PATENT DOCUMENTS

| | | |
|---|---|---|
| DE | 196 29 070 A | 2/1993 |
| EP | 0 065 827 A | 12/1982 |
| WO | WO 84/01879 | 5/1984 |
| WO | WO 00/25705 | 5/2000 |

OTHER PUBLICATIONS

"Calcification of Subcutaneously Implanted Type I Collagen Sponges Effects of Formaldehyde and Flutaraldehyde Pretreatments", by, Levy et al., American Journal of Pathology, vol. 122, No. 1, Jan. 1986, pp. 71–82.

"Ectopic Calcification; Gathering Hard Facts About Soft Tissue Mineralization", by, Cecilia M. Giachelli, American Journal of Pathology, vol. 154, No. 3, Mar. 1999, pp. 671–675.

International Search Report dated Jun. 12, 2001 for International Application No. PCT/US00/35141.

*Primary Examiner*—Cary E. O'Connor
(74) *Attorney, Agent, or Firm*—Patterson, Thuente, Skaar & Christensen, P.A.; Peter S. Dardi; Hallie A. Finucane

(57) ABSTRACT

Crosslinked tissue is contacted with one or more toxicity reducing solutions to remove cytotoxicity associated with the crosslinking process. In particular, crosslinked tissue can be contacted with an inorganic sulfur-oxygen group to form chemical adducts of aldehydes and the inorganic sulfur-oxygen group. Preferably, the cytotoxicity reduced crosslinked tissue has no residual cytotoxicity. In preferred embodiments, a plurality of toxicity reducing agents are used to detoxify the tissue. Preferred toxicity reducing agents include, for example, inorganic sulfur-oxygen ions, such as bisulfate and thiosulfate, organic sulfates, amines, ammonia/ammonium, and surfactants.

33 Claims, 1 Drawing Sheet

U.S. PATENT DOCUMENTS

| | | | |
|---|---|---|---|
| 5,104,405 A | 4/1992 | Nimni | 623/2 |
| 5,188,834 A | 2/1993 | Grimm et al. | 424/422 |
| 5,215,541 A | 6/1993 | Nashef et al. | 8/94.11 |
| 5,368,608 A | 11/1994 | Levy et al. | 9/94.11 |
| 5,397,353 A | 3/1995 | Oliver et al. | 623/11 |
| 5,447,536 A | 9/1995 | Girardot et al. | 8/94.11 |
| 5,476,516 A | 12/1995 | Seifter et al. | 8/94.11 |
| 5,509,932 A | 4/1996 | Keogh et al. | 623/11 |
| 5,549,666 A | 8/1996 | Hata et al. | 623/2 |
| 5,554,184 A | 9/1996 | Machiraju | 623/2 |
| 5,558,875 A | 9/1996 | Wang | 424/422 |
| 5,578,452 A | 11/1996 | Shi et al. | 435/7.21 |
| 5,645,587 A | 7/1997 | Chanda et al. | 623/11 |
| 5,674,298 A | 10/1997 | Levy et al. | 8/94.11 |
| 5,679,112 A | 10/1997 | Levy et al. | 8/94.11 |
| 5,697,972 A | 12/1997 | Kim et al. | 623/2 |
| 5,733,339 A | 3/1998 | Girardot et al. | 8/94.11 |
| 5,746,775 A | 5/1998 | Levy et al. | 8/94.11 |
| 5,782,931 A | 7/1998 | Yang et al. | 8/94.11 |
| 5,855,620 A | 1/1999 | Bishopric et al. | 623/11 |
| 5,862,806 A | 1/1999 | Cheung | 128/898 |
| 5,873,812 A | 2/1999 | Ciana et al. | 600/36 |
| 5,879,383 A | 3/1999 | Bruchman et al. | 623/1 |
| 5,882,850 A | 3/1999 | Khor et al. | 435/1 |
| 5,891,196 A | 4/1999 | Lee et al. | 8/94.11 |
| 5,911,951 A | 6/1999 | Girardot et al. | 422/28 |
| 5,916,265 A | 6/1999 | Hu | 623/11 |
| 5,919,472 A | 7/1999 | Trescony et al. | 424/422 |
| 5,931,969 A | 8/1999 | Carpentier et al. | 8/94.11 |
| 5,935,168 A | 8/1999 | Yang et al. | 623/11 |
| 6,132,986 A * | 10/2000 | Pathak et al. | 435/40.5 |
| 6,171,344 B1 * | 1/2001 | Atala | 623/23.72 |
| 6,214,055 B1 * | 4/2001 | Simionescu et al. | 623/23.72 |
| 6,267,786 B1 * | 7/2001 | Stone | 623/23.72 |
| 6,322,593 B1 | 11/2001 | Pathak et al. | 623/23.72 |

* cited by examiner

BIOCOMPATIBLE PROSTHETIC TISSUE

BACKGROUND OF THE INVENTION

The invention relates to medical articles including an aldehyde crosslinked tissue. In particular, the invention relates to fixed tissue with reduced cytotoxicity and reduced susceptibility to calcification.

Various medical articles have been designed particularly for contact with a patient's bodily fluids. This contact can be sufficiently long such that surface interactions between the medical article and the patient's blood and/or tissue become significant. For example, the host interaction with the medical article can lead to degradation, such as calcification of the medical article. Relevant medical articles include, for example, catheters and prostheses.

Catheters include percutaneous devices that penetrate the skin to provide access to a bodily system. Prostheses, i.e., prosthetic devices, are used to repair or replace damaged or diseased organs, tissues and other structures in humans and animals. Prostheses must be generally biocompatible since they are typically implanted for extended periods of time. Prostheses can be constructed from natural materials, synthetic materials or a combination thereof.

Bioprosthetic heart valves from natural materials were introduced in the early 1960's. Bioprosthetic heart valves typically are derived from pig aortic valves or are manufactured from other biological materials such as bovine pericardium. Xenograft heart valves, i.e., heart valves originating from a donor of a species different from the species of the recipient, are typically fixed with glutaraldehyde prior to implantation to reduce the possibility of immunological rejection. Glutaraldehyde reacts to form covalent bonds with free functional groups in proteins, thereby chemically crosslinking nearby proteins.

The importance of bioprosthetic animal heart valves as replacements for damaged or diseased human heart valves has resulted in a considerable amount of interest in the long term performance of these valves and, in particular, in the effects of calcification on these xeno-transplants. Calcification, i.e., the deposit of calcium salts, especially calcium phosphate (hydroxyapatite), can occur in and on some materials of a medical article while contacting the patient's bodily fluids or tissue. Calcification can affect the performance and structural integrity of medical articles constructed from these materials, especially over extended periods of time. For example, calcification is the primary cause of clinical failure of bioprosthetic heart valves made from porcine aortic valves or bovine pericardium. Calcification can be particularly severe at stress points, such as where suture passes through tissue.

Generally, bioprosthetic heart valves begin failing after about seven years following implantation, and few bioprosthetic valves remain functional after 20 years. Replacement of a degenerating valve prosthesis subjects the patient to additional surgical risk, especially in the elderly and in situations of emergency replacement. While failure of bioprostheses is a problem for patients of all ages, it is particularly pronounced in younger patients. Over fifty percent of bioprosthetic valve replacements in patients under the age of 15 fail in less than five years because of calcification. Other prostheses made from natural and/or synthetic materials may also display clinically significant calcification.

As a result, there is considerable interest in preventing the deposit of calcium on implanted biomaterials, especially heart valves. Research on the prevention of calcification has focused to a considerable extent on the pretreatment of the biomaterial prior to implantation. Detergents (e.g., sodium dodecyl sulfate), toluidine blue or diphosphonates have been used to pretreat tissues in an attempt to decrease calcification by reducing calcium nucleation. Within a relatively short time, these materials tend to wash out of the bioprosthetic material into the bodily fluids surrounding the implant, limiting their effectiveness. A significant advance toward reducing calcification of bioprostheses was the determination that $Al^{+3}$ cations and other multivalent cations inhibit calcification.

Other approaches to reducing calcification have employed a chemical process in which at least some of the reactive glutaraldehyde moieties are inactivated. Still other approaches have included development of alternative fixation techniques, since evidence suggests that the fixation process itself may contribute to calcification and the corresponding mechanical deterioration. In addition, since non-viable cells present in transplanted tissue are sites for calcium deposition, various processes have been developed to remove cellular material from the collagen-elastin matrix of the tissue prior to implantation.

Another major disadvantage of tissue based prostheses is the failure of such devices to be self-maintaining. Long term durability is enhanced by the ability of viable cells to populate the implanted tissue and to carry out maintenance functions. The importance of viable cells has been studied in the context of homograft transplants, i.e., transplants from one member of a species to another member of the same species. Proper homograft preservation can maximize the number of viable cells remaining in the tissue as determined by matrix protein synthesis. Preservation techniques that do not promote cell survival, such as long term storage at 4° C., are associated with reduced in vivo durability and increased reoperation rates.

Thus cell ingrowth into prosthetic tissue material can decrease the prevalence of calcification and reintroduce some degree of self maintenance. However, aldehyde crosslinking tends to make the tissue cytotoxic. This cytotoxicity appears to be due to unreacted aldehyde functional groups. While processing approaches to reduce calcification may reduce the level of cytotoxicity, residual cytotoxicity remains a problem with respect to colonization of the crosslinked tissue by mammalian cells both in vitro in a cell culture and in vivo in a patient following implantation.

SUMMARY OF THE INVENTION

In a first aspect, the invention pertains to a prosthetic tissue comprising a chemically crosslinked protein matrix having no detectable cytotoxicity without any added growth hormones.

In a further aspect, the invention pertains to a prosthetic tissue comprising a protein matrix crosslinked with a multifunctional aldehyde having an extractable residual aldehyde compound concentration of no more than about $5 \times 10^{-4}$ moles aldehyde per gram of dry tissue.

Moreover, the invention pertains to a prosthetic tissue comprising adducts of aldehyde groups and inorganic sulfur-oxygen groups.

In addition, the invention pertains to a prosthetic tissue comprising adducts of aldehyde groups and ammonia/ammonium groups and adducts of aldehyde groups and sulfur-oxygen groups.

In another aspect, the invention pertains to a method for reducing residual reactive aldehyde groups associated with an aldehyde crosslinked tissue. The method includes contacting an aldehyde crosslinked tissue with an inorganic sulfur-oxygen compound.

Furthermore, the invention pertains to a composition comprising inorganic sulfur-oxygen group and an amine.

DETAILED DESCRIPTION OF THE ILLUSTRATIVE EMBODIMENTS

Figure 1:
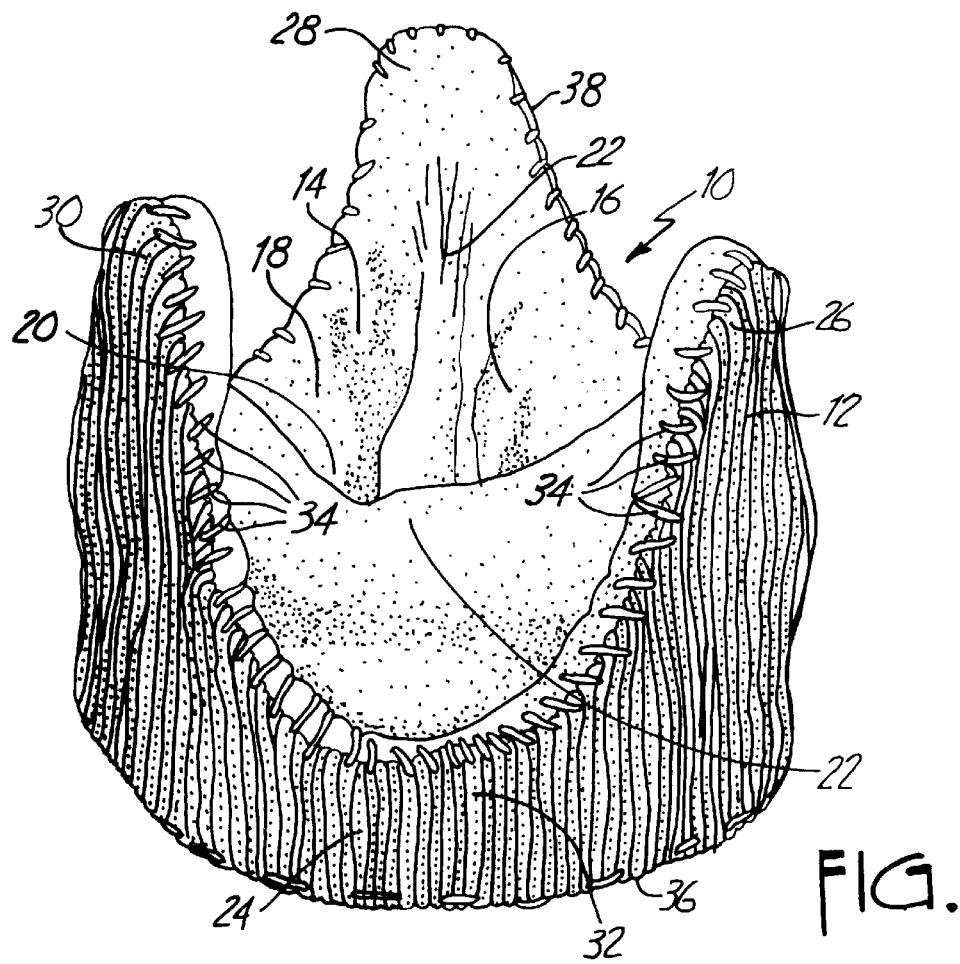
FIG. 1 is a perspective view of a tissue based heart valve bioprosthesis.

It has been discovered that a combination of treatments to reduce, or preferably eliminate, cytoxicity of aldehyde crosslinked tissue provides synergistic improvement in the reduction of cytotoxicity. In particular, agents that can reduce cytotoxicity can be combined with other agents that are able to remove some or all of the residual cytotoxicity. Preferred combinations of agents result in aldehyde crosslinked tissue with no observable cytotoxicity, no measurable multifunctional aldehyde activity and sharply reduced formaldehyde activity, if applicable. In addition, it has been discovered that inorganic sulfur-oxygen anions are useful as a toxicity reducing agent alone or in combination with other toxicity reducing agents. The crosslinked tissue with reduced or eliminated cytotoxicity is expected to have corresponding reductions in calcification upon implantation into the patient.

In general, relevant medical devices are bioprostheses that are formed to mimic a corresponding structure within the body. The bioprostheses can be used to replace the corresponding native structure. The medical device, can be prosthetic devices or components suitable for long term implantation within a recipient patient. Generally, the patient is an animal, preferably a mammal, such as a human. The medical devices include an aldehyde crosslinked tissue. The crosslinked tissue is treated with a combination of agents to reduce and preferably eliminate cytotoxicity.

Cytotoxicity or toxicity is used herein to describe a detrimental or destructive affect on cells. Suitable tissue for application of the cytotoxicity reducing agents includes a wide range of structures with an aldehyde crosslinked network of extracellular matrix proteins. Natural tissues can be relatively intact or decellularized tissues. Preferred aldehyde crosslinking agents are multifunctional aldehydes, especially difunctional aldehydes, such as glutaraldehyde.

The toxicity reducing agents can be grouped as inorganic sulfur-oxygen anions, organic sulfate compounds, ammonia ($NH_3$)/ammonium ions ($NH_4^+$), amines, and surfactants. Relevant inorganic sulfur-oxygen agents include inorganic sulfur-oxygen anions, such as sulfate ($SO_4^{-2}$), thiosulfate ($S_2O_3^{-2}$) and bisulfate ($HSO_4^{-1}$). Organic sulfate compounds include, for example, methyl sulfate ($CH_3OSO_2OH$) and the like. Amines include primary amines, secondary amines, tertiary amines and quaternary amines. Preferred amines include amino acids, such as glycine. Preferred surfactants include nonionic surfactants, such as polysorbates.

Preferred combinations of toxicity reducing agents include the combination of an inorganic sulfur-oxygen anion and an amine. In a more preferred embodiment, this aldehyde crosslinked tissue is treated with an inorganic sulfur-oxygen anion, an amine and a surfactant. In especially preferred embodiments, the aldehyde crosslinked tissue is treated with an inorganic sulfur-oxygen anion, an amine, a surfactant and ammonia/ammonium ions. Furthermore, the inorganic sulfur-oxygen anions can include a combination of thiosulfate and bisulfate.

After the aldehyde crosslinked tissue is treated with the toxicity reducing agents to remove toxins, the tissue can be populated or repopulated. The population of the tissue can be performed in vivo or in vitro using a cell culture or the like. Using the patient's own cells to populate the substrate in vitro lessens the possibility of rejection of the prosthesis by the patient's immune system. The in vivo population of the tissue results in cellular attachment from the patient's blood or tissue following implantation of the prosthesis.

While less effective treatments to remove cytotoxicity of aldehyde crosslinked tissue can be sufficient to allow some cellular attachment with the tissue, more effective toxin removal described herein provides for more effective cellular proliferation with the crosslinked, tissue matrix. This may be particularly advantageous for cellularization of the tissue under shear forces, which can be found in blood vessels and in some cell culture systems. Since shear forces can inhibit initial cellular attachment, more effective cytotoxicity removal can result in stronger cellular attachment. Shear forces can lead to stronger adhesion between the cells and the crosslinked protein matrix by stimulating cellular production of adhesion compounds. Tissue with viable cells is self maintaining with respect to upkeep of the extracellular matrix. Furthermore, the removal of reactive aldehyde groups would be expected to reduce the risk of calcification directly and indirectly by encouraging colonization by cells that inhibit the calcification process.

The crosslinked tissue treated with the improved compositions described herein can be incorporated into a comprehensive tissue engineering program. In particular, the crosslinked tissue can be associated with compounds, especially proteins, that encourage attachment of cells to the tissue. Similarly, the crosslinked tissue can be associated with growth factors that encourage proliferation of cells that become attached to the tissue.

Medical Devices

Relevant medical devices generally include a crosslinked tissue material. The crosslinked tissue is suitable for cellular attachment. Generally, these medical devices are prostheses or components designed for implantation into or onto a patient for extended periods of time. Prostheses include, for example, artificial hearts, artificial heart valves, annuloplasty rings, pericardial patches, vascular and structural stents, vascular grafts or conduits, pledgets, suture, permanently in-dwelling percutaneous devices, vascular shunts, dermal grafts for wound healing, and surgical patches. "Vascular" sites and structures as used herein include cardiovascular sites and structures and other blood contacting sites and structures. Biomedical devices that are designed to dwell for extended periods of time within a patient are also relevant for modification as described herein. These devices include, for example, Hickman catheters.

Particularly preferred medical devices include tissue based heart valve prostheses, vascular grafts and pericardial patches. Tissue based heart valve prostheses can be stented, in which a stent serves as a frame for tissue based leaflets, or stentless, in which a tissue heart valve is implanted utilizing the recipient's native support structure, i.e., the aorta or mitral annulus. An aortic heart valve bioprosthesis is shown in FIG. 1. Aortic valve 10 includes a cover 12 and a harvested heart valve 14. Heart valve 14 has three leaflets 16, 18, 20 meeting at commissures 22. Cover 12 has a generally annular base 24 and three commissure supports 26, 28, 30. Commissure supports 26, 28, 30 meet at connecting portions 32. Sutures 34 are located along inflow edge 36 and outflow edge 38 to secure cover 12, to harvested heart valve 14.

Figure 2:
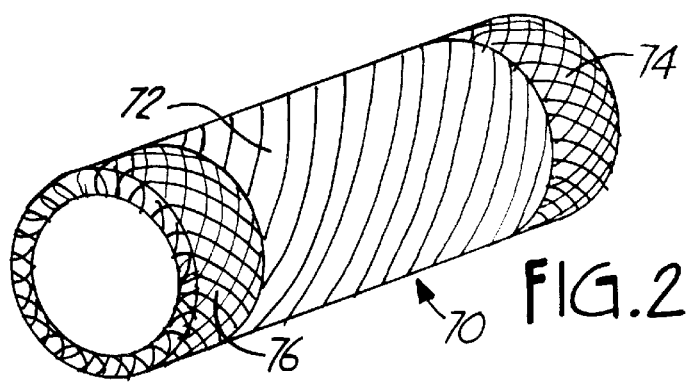
FIG. 2 is a perspective view of a vascular graft.
Figure 3:
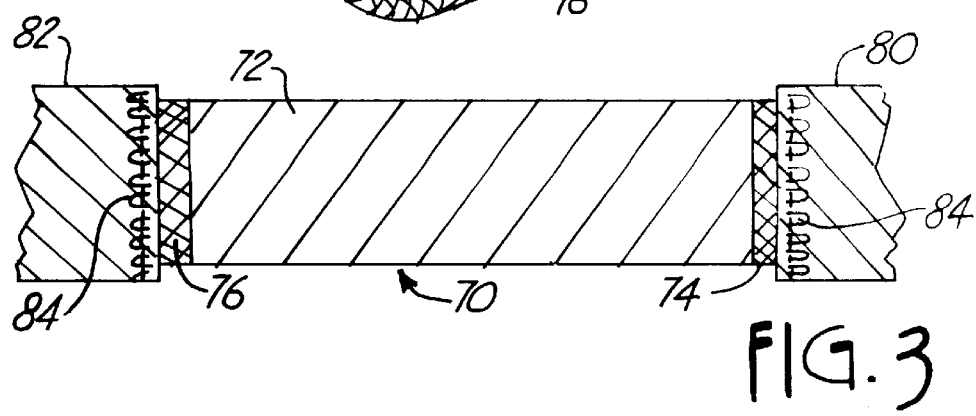
FIG. 3 is a side view of the vascular graft of FIG. 2 attached to a blood vessel.

A representative vascular graft 70 is depicted in FIG. 2. Vascular graft 70 includes a flexible tubular structure 72 and optional sewing cuffs 74, 76. Flexible tubular structure 72 can include one or more biocompatible materials, such as tissue, synthetic polymer or combinations thereof. Sewing cuffs 74, 76 are formed from fabric, tissue or the like. Sewing cuffs 74, 76 assist with the implantation of the prosthesis and may provide reinforcement of the prosthesis at the site of anastomoses, i.e., attachment of the vessel to the graft. A side view of vascular graft 70 attached to natural vessel sections 80, 82 is depicted in FIG. 3. As shown in FIG. 3, suture 84 is used to secure vascular graft 70 to vessel sections 80, 82.

The medical devices include crosslinked tissue material, as described in the following section. The medical devices can also include other biocompatible materials, such as polymers, ceramics and metals. Appropriate ceramics include, without limitation, hydroxyapatite, alumina and pyrolytic carbon. Biocompatible metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, and Nitinol®, a nickel-titanium alloy.

Polymeric materials can be fabricated from synthetic polymers as well as purified biological polymers. Appropriate synthetic materials include hydrogels and other synthetic materials that cannot withstand severe dehydration. Suitable polymers include bioresorbable polymers that are gradually resorbed after implantation within a patient.

Appropriate synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers. These synthetic polymeric materials can be formed into fibers or yarns and then can be woven or knitted into a mesh to form a matrix or substrate. Alternatively, the synthetic polymer materials can be molded or cast into appropriate forms.

Biological polymers can be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Crosslinked Tissue Material

Appropriate crosslinked bioprosthetic tissue materials can be formed from natural materials, synthetic tissue matrices and combinations thereof. "Bioprosthesis" is used in a broad sense to include prosthetic comprised of a natural material component that is joined together with other natural or synthetic materials. Synthetic tissue matrices can be formed from extracellular matrix proteins that are crosslinked to form a tissue matrix. Extracellular matrix proteins are commercially available. Natural, i.e. biological, material for use in the invention includes relatively intact tissue as well as decellularized tissue. These tissues may be obtained from, for example, native heart valves, portions of native heart valves such as roots, walls and leaflets, pericardial tissues such as pericardial patches, connective tissues, bypass grafts, tendons, ligaments, skin patches, blood vessels, cartilage, dura mater, skin, bone, fascia, submucosa, umbilical tissues, and the like.

Natural tissues are derived from a particular animal species, typically mammalian, such as human, bovine, porcine, canine, seal or kangaroo. These tissues may include the whole organ, including homografts and autografts. These natural tissues generally include collagen-containing material. Natural tissue is typically, but not necessarily, soft tissue. Tissue materials are particularly useful for the formation of tissue heart valve prostheses. The tissue can be decellularized. Decellularization approaches are described, for example, U.S. Pat. No. 5,855,620 to Bishopric et al., entitled "Matrix Substrate for a Viable Body Tissue-Derived Prosthesis and Method for Making the Same," incorporated herein by reference, and in published PCT Application WO96/03093, incorporated herein by reference.

Tissues can be fixed by crosslinking. Fixation provides mechanical stabilization, for example, by preventing enzymatic degradation of the tissue. Glutaraldehyde, formaldehyde or a combination thereof is typically used for fixation, but other fixatives can be used, such as epoxides and other difunctional aldehydes. Aldehyde functional groups are highly reactive with amine groups in proteins, such as collagen.

The chemical nature of the glutaraldehyde-amine reaction is complex due to the reactivity of the glutaraldehyde molecule as well as the self-polymerization of dialdehydes. The most important component of the reaction products of an aldehyde and a primary amine involves the formation of a Schiff's base wherein the nitrogen forms a double bond with the aldehyde carbon, replacing the double bond with the oxygen. However, a variety of complex structures can be formed with free aldehyde groups. The chemistry of glutaraldehyde crosslinking is described further in "Bioprosthesis derived crosslinked and chemically modified collagenous tissues," in Collagen, vol. III, Nimni et al., Eds. pp. 1–38 (CRC Press, Boca Raton, Fla., 1988), incorporated herein by reference.

Dialdehydes, including glutaraldehyde, may be self-polymerizing. Improved crosslinking results may be obtained with moderate sized glutaraldehyde oligomers that more closely match the distance between collagen fibers. There are a variety of ways of adjusting the distribution of glutaraldehyde oligomers. For example, the concentration can be lowered to yield an equilibrium distribution with an increased number of smaller oligomers. Alternatively, a selectively permeable membrane can be used to exclude larger glutaraldehyde oligomers from the vicinity of the tissue to be crosslinked. Improved results obtained by crosslinking with a selectively permeable membrane is described further in copending and commonly assigned U.S. Pat. No. 5,958,669 to Ogle et al., entitled "Tissue Fixation With Crosslinking Compounds," incorporated herein by reference.

Formaldehyde generally does not function as a satisfactory crosslinking agent. However, formaldehyde is a common sterilant used to store tissue following glutaraldehyde crosslinking. Ethanol is another common sterilant component for crosslinked tissue.

The crosslinked tissue material can form the entire medical device or it can form portions of the medical device. Similarly, different portions of crosslinked tissue material can be combined to form the medical device.

Toxicity Reducing Agents and Treatment of Crosslinked Tissue

Toxicity reducing agents include, for example, inorganic sulfur-oxygen compounds, organic sulfate compounds, amines, ammonia/ammonium ions and surfactants. Many toxicity reducing agents act by forming a chemical adduct with the aldehyde functional groups. For example, sulfate compounds can undergo nucleophilic addition to the carbonyl (C=O) group of an aldehyde. In some preferred embodiments, combinations of toxicity reducing agents are used to contact the tissue either sequentially or simultaneously. Suitable combinations of toxicity reducing agents can be used to effectively reduce aldehyde reactivity within aldehyde crosslinked tissue.

Preferred toxicity reducing agents generally include inorganic sulfur-oxygen anions or corresponding compounds. Preferred combinations of toxicity reducing agents include an amine and inorganic sulfur-oxygen ions. More preferred combinations of toxicity reducing agents further include a surfactant and/or ammonium ions. Furthermore, a plurality of inorganic sulfur-oxygen anions, e.g., sulfates (bisulfates) and thiosulfates, can be combined to treat the crosslinked tissue. These toxicity reducing agents can be used to effectively reduce or eliminate residual cytotoxicity of the crosslinked tissue and to lower measurable residual aldehyde reactivity.

As used herein "inorganic sulfur-oxygen anions" include, for example, sulfate anions $SO_4^{-2}$ and thiosulfate anions $S_2O_3^{-2}$, as well as protonated forms thereof, e.g., bisulfate ($HSO_4^-$). The protonated and deprotonated forms are in equilibrium in aqueous solution with the relative amounts of each form depending on the pH. Thiosulfates are known to react with aldehyde groups to form an addition product, i.e., adduct, according to the reaction $RCO+HSO_3 \rightleftharpoons RC(OH)SO_3^-$. Particularly good results with respect to removal of aldehyde functionality have been obtained with a mixture of sulfate/bisulfate anions and thiosulfate anions, as described in the Examples below.

Additional toxicity reducing agents include organic substituted sulfates, such as aliphatic sulfates including, for example, methyl sulfate $CH_3O_4S^-$, dimethyl sulfate $(CH_3)_2O_4S$ and dodecyl sulfate $CH_3(CH_2)_{11}O_4S^-$, as well as protonated forms thereof, e.g., methyl hydrogen sulfate $CH_4O_4S$. The treatment of glutaraldehyde crosslinked tissue with aliphatic sulfates with 7 to 18 carbon atoms is described in U.S. Pat. No. 4,323,358 to Lentz et al., entitled "Method for Inhibiting Mineralization of Natural Tissue During Implantation," incorporated herein by reference.

Amines generally can undergo nucleophilic addition at aldehyde functional groups to form an adduct. In particular, ammonia ($NH_3$ or ammonium ions $NH_4^+$) and primary amines ($R_1NH_2$) can react with aldehydes ($R_2CH=O$) to form stable imines ($R_2CH=NR_3$, $R_3=R_1$ or H), in which the double bonded oxygen is replaced with a double bond to the amine nitrogen. Imines formed with ammonia or ammonium ions are subject to further reaction with another aammonia/ammonium to form a di-primary amine, which then can further react with additional aldehydes. Two hydrogens of the primary amine or ammonia are replaced by the double bond to the aldehyde carbon. Secondary amines ($R_4R_5NH$) cannot form neutral imines, although they can form transient cationic imines ($R_2CH=N^+R_4R_5$), which can undergo nucleophilic addition by a nucleophile ($HR_6$) to form stable substituted amines ($R_2CR_6H-NR_4R_5$) with the nucleophile of $R_6$, such as an O, N or S, replacing the aldehyde oxygen.

The amines can be multifunctional compounds, such as 1,6 hexane diamine and N,N,N',N'-tetramethylene diamine. The use of diamines as an anticalcification agent is described in, for example, U.S. Pat. No. 5,104,405 to Nimni, entitled "Process for Improving the Biostability of Tissue Implant Devices and Bioprosthetic Implants so Produced," incorporated herein by reference, and U.S. Pat. No. 5,447,536 to Girardot et al., entitled "Method for Fixation of Biological Tissue," incorporated herein by reference.

Similarly, amino acids can be a source of primary amines. Preferred amino acids include, for example, glycine, lysine, aspartic acid, glutamic acid, aspartic acid and derivatives thereof, such as hydroxy lysine. Amino acids have been used as anticalcification agents, as described, for example, in U.S. Pat. No. 5,188,834 to Grimm et al., entitled "Method of Preparing a Biological Implantation Material," incorporated herein by reference.

In addition, preferred treatment compositions include a surfactant, preferably a nonionic surfactant. Suitable nonionic surfactants include, for example, polyoxyalkylene ethers, polyoxyalkylene alkylaryl ethers, aliphatic esters, polyethers, polyoxyalkylene ester derivatives, saccharide ester derivatives and combinations thereof. Preferred nonionic polyoxyalkylene ethers, including polyoxyethylene ethers, include a relatively long hydrophobic hydrocarbon group joined at a hydroxyl group or an aryl group with alkalene oxide groups. Specific suitable polyoxyalkylene ethers include, for example, polyoxyethylene lauryl ether, polyoxyethylene oleyl ether, polyoxyethylene cetyl ether, polyethylene glycol p-isooctyl phenyl ethers, such as Triton X-100, and the like.

Nonionic aliphatic esters include, for example, aliphatic fatty acid esters, polypropyleneglycol fatty acid esters such as propyleneglycol monostearate and glycerol fatty acid esters, such as glycerol monostearate. Aliphatic fatty acid esters include compounds having a chemical formula $R_4COOR_5$, where $R_4$ is a hydrocarbon chain from a fatty acid generally with about 8 to about 20 carbon atoms, and $R_5$ is an aliphatic group from an alcohol generally with about 1 to about 5 carbon atoms.

Suitable nonionic surfactants further include sorbitol or other sugars formed into ester linkages with fatty acids. The surfactants formed with sorbitol include, for example, sorbitan trioleate, sorbitan stearate, sorbitan laurate and sorbitan monooleate. Similarly, nonionic surfactants can be formed from fatty acid esters with polyoxyethylene compounds. Examples of these esters include, for example, polyoxyethylene monooleate and polyoxyethylene monostearate. Preferred nonionic surfactants include, for example, polyoxyethylene sorbitan esters which include polyoxyethylene compounds in an ether linkage with sorbital and an ester with a fatty acid. Particularly preferred nonionic surfactants include, for example, Polysorbate 80 or polyoxyethylene (20) sorbitan monooleate which are sold under the trade name Tween® 80.

The toxicity reducing agents or compounds are dissolved into an aqueous solution for use. Preferred compositions comprise a plurality of toxicity reducing agents, as described above. In other words, in preferred embodiments, the crosslinked tissue is simultaneously contacted with a plurality of toxicity reducing agents. Alternatively, the crosslinked tissue can be treated sequentially with the plurality of toxicity reducing compounds. If three or more toxicity reducing agents are used, the crosslinked tissue can be contacted with the toxicity reducing agents simultaneously, sequentially or a combination thereof with individual agents and groups of agents applied sequentially.

Preferred toxicity reducing solutions include inorganic sulfur-oxygen compounds/anions in a concentration from about 0.025 molar (M) to about 1.0M, preferably from about 0.035M to about 0.5M, more preferably from about 0.05M to about 0.1M. In particularly preferred compositions, the solutions include both sulfate/bisulfate anions and thiosulfate anions, with the sulfate/bisulfate anions in a concentration range from about 0.005M to about 0.5M, preferably from about 0.01M to about 0.25M, and more preferably from about 0.015M to about 0.1M, and the thiosulfate anions in a concentration range from about 0.005M to about 0.5M, preferably from about 0.01M to about 0.25M, and more preferably from about 0.02M to about 0.125M.

Preferred toxicity reducing solutions include, for example, an amine in a concentration range from about 0.005M to about 3M, preferably from about 0.1M to about 2.5M, and more preferably from about 0.25M to about 2.0M. As noted above, preferred amines include amino acids. Furthermore, preferred toxicity reducing solutions include ammonium ions at a concentration from about 0.01M to about 3M, preferably from about 0.05M to about 2M, and more preferably from about 0.1M to about 1M. In addition, preferred toxicity reducing solutions include nonionic surfactants at a concentration from about $1 \times 10^{-4}$M to about 0.5M, preferably from about $5 \times 10^{-4}$M to about 0.015M, and more preferably from about $1 \times 10^{-3}$M to about 0.01M.

While some of the toxicity reducing compounds may buffer the solution, an additional buffer can be added. If a plurality of toxicity reducing solutions are used, each can be buffered with suitable buffers. In particular, a toxicity reducing solution preferably is buffered at a near physiological pH ranging from about 6.0 to about 10.0, and more preferably ranging from about 6.9 to about 9.0. Suitable buffers can be based on, for example, the following compounds: ammonium, phosphate, borate, bicarbonate, carbonate, cacodylate, citrate, and other organic buffers such as tris (hydroxymethyl) aminomethane (TRIS), N-(2-hydroxyethyl) piperazine-N'-(2-ethanesulfonic acid) (HEPES), and morpholine propanesulphonic acid (MOPS).

The toxicity reducing solution can include other optional components including anticalcification agents and other toxicity reducing agents. Other optional ingredients of particular interest include alcohols, especially ethanol. If used, the solution generally includes greater than about 50 weight percent ethanol. Ethanol treatment, followed by extensive rinsing of the crosslinked tissue in an aqueous solution, is known to reduce cytotoxicity and to reduce calcification of glutaraldehyde crosslinked tissue.

In preferred embodiments, the crosslinked tissue is simultaneously contacted with the desired toxicity reducing agents in a single toxicity reducing solution. Alternatively, the crosslinked tissue can be treated sequentially with a plurality of toxicity reducing solutions, each toxicity reducing solution containing one or more toxicity reducing agents.

Once all of the ingredients of the toxicity reducing solution have been combined, each toxicity reducing solution preferably is sterilized to remove any bacterial contaminants that could contaminate the tissue upon contact with the solution.

The tissue can be crosslinked and stored in an aqueous glutaraldehyde solution as a sterilant until the tissue is ready to be treated with the toxicity reducing solution. Then, the tissue is removed from the solution and placed within the toxicity reducing solution. Preferably, the crosslinked tissue is rinsed with sterile saline prior to placement in the toxicity reducing solution. Preferably, the tissue is kept in each toxicity reducing solution for at least about 30 minutes, more preferably at least about 2 hours, and even more preferably at least about 4 hours. The tissue can be kept in the toxicity reducing solution for 24 hours, even several days, and the crosslinked tissue can be stored in the toxicity reducing solution for longer periods of time. The tissue can be stored in a toxicity reducing solution until used.

Properties of Cytotoxicity Reduced Tissue

Aldehyde crosslinked tissue can be toxic with respect to microorganisms as well as mammalian cells, i.e., cytotoxic. It is thought that this cytotoxicity may be due to slow leaching or extraction of uncrosslinked aldehydes from the crosslinked tissue and/or due to unreacted aldehyde functional groups within the crosslinked aldehyde network. The cytotoxicity reduction approaches described above reduce any residual aldehyde functionality regardless of the source of the aldehyde functionality.

Preferred cytotoxicity reduction approaches remove all detectable cytotoxicity with respect to the crosslinked tissue. Thus, the tissue following cytotoxicity reduction is well suited for colonization with cells to form a recellularized tissue. The recellularization can be performed in vitro or in vivo, as described further below.

While cytotoxicity is reduced, it is difficult to quantify any residual cytotoxicity or related effects due to possible reduced levels of aldehyde reactivity based on visual observation of cell growth. However, small residual aldehyde functionality may affect the degree of cellular attachment, the incorporation of cells into the crosslinked tissue matrix, and/or other more subtle effects on cellular proliferation and metabolism. More quantitative measurements can be made directly on the amount of remaining aldehyde functionality. In addition, microorganisms can be used to examine cytotoxicity since some microorganisms may be more sensitive than mammalian cells to aldehyde reactivity. Thus, visual observation with selected microorganisms can be used to detect visually lower levels of aldehyde toxicity.

Cytotoxicity of the treated tissue can be evaluated by examining the possibility of growing microorganisms in the presence of the tissue. To perform the evaluation, the treated tissue samples are placed into a sterile media suitable for growing desired microorganisms, e.g., fungi and/or bacteria. Microorganisms tend to be more sensitive to toxins than eukaryotic cells, although in any particular case, the relative sensitivity to toxins depends on the toxin and the microorganism. Thus, a plurality of microorganisms can be used to reduce the variability of the results. Once the tissue is contacted with the appropriate culture media, the sample is inoculated with the microorganism. Then, the inoculated container is incubated at an appropriate temperature for microbial, i.e., fungal and/or bacterial, growth for approximately three to five days. Growth can be compared between samples with no tissue and samples with tissue to evaluate the cytotoxicity of the tissue.

With respect to measurements of residual aldehyde reactivity in the treated tissue samples, both extractable formaldehyde reactivity and extractable glutaraldehyde, i.e., multifunctional aldehyde, reactivity can be measured independently. Generally, the tissues are contacted with a sterilizing solution, such as a mixture of aldehydes and ethanol, after glutaraldehyde crosslinking. Formaldehyde forms a reversible chemical crosslink with certain protein functional groups. Residual formaldehyde may remain associated with the tissue subsequent to glutaraldehyde crosslinking. Furthermore, residual ethanol reactivity can also be measured since ethanol can also contribute to cytotoxicity. A measure of the remaining reactivity of the crosslinking compounds and alcohol is determined by measuring the amount of extractable compounds. Extraction is determined following incubation of the tissue in a solution, such as water, with, preferably, shaking or mixing.

The presence of formaldehyde and glutaraldehyde can be detected by high-performance liquid chromatography (HPLC). Samples can be diluted with very pure reverse osmosis water with a residual electrical resistance of less than about 16 megaohms. Evaluation of the concentration is performed by using a standard curve. The standards are run using the same processing conditions as the samples. Values for the samples can then be evaluated by interpolating between values used to generate the standard curve. Glutaraldehyde and formaldehyde can be distinguished based on their retention times. Similarly, ethanol can be quantitifed using gas chromatography. These procedures are described with respect to particular experiments in the examples below.

In preferred embodiments, extractable formaldehyde is less than about $2 \times 10^{-3}$ moles formaldehyde per gram dry tissue, preferably less than about $1 \times 10^{-3}$ moles per gram dry tissue, more preferably less than about $5 \times 10^{-4}$ moles per gram dry tissue, even more preferably from about $1 \times 10^{-4}$ moles to about $2 \times 10^{-4}$ moles formaldehyde per gram dry tissue. Similarly, extractable glutaraldehyde is less than about $6 \times 10^{-5}$ moles glutaraldehyde per gram of dry tissue, more preferably less than about $2 \times 10^{-5}$ moles per gram dry tissue, and even more preferably less than about $1 \times 10^{-5}$ moles glutaraldehyde per gram of dry tissue. Also, the residual extractable ethanol in preferred embodiments is less than about 0.02 moles ethanol per gram of dry tissue, more preferably less than about $6.5 \times 10^{-3}$ moles per gram of dry tissue and even more preferably less than about $3 \times 10^{-3}$ moles per gram of dry tissue.

Colonization of the Tissue With Cells

Once the crosslinked tissue is treated with the toxicity reducing agents, it is particularly suitable for in vivo or in vitro affiliation of cells with the crosslinked tissue. To accomplish in vivo affiliation with the tissue, the treated tissue is implanted into a patient. Since the cytotoxicity of the crosslinked tissue is reduced or eliminated, the tissue is suitable seeding ground for cell colonization by cells that are circulating in the patient's fluids. Thus, circulating cells of the patient affiliate with the tissue and can form a repopulated tissue material.

The in vitro affiliation of cells with the crosslinked tissue is accomplished in a cell culture system. In order to reduce the possibility of transplant rejection, the mammalian cells used for in vitro colonization preferably are autologous cells, i.e., cells from the ultimate recipient. In vitro affiliation of cells with crosslinked tissue following cytotoxicity reduction preferably is performed at hospitals where the patient's cells can be removed for use in a cell culture system. Preferred cells include endothelial cells and fibroblast precursor cells. Association of endothelial cells is particularly appropriate in the production of prostheses that replace structures that naturally have an endothelial or epithelial cell lining, such as vascular components, cardiovascular structures, portions of the lymphatic system, uterine tissue or retinal tissue. Fibroblasts are collagen secreting cells that maintain the extracellular matrix. They are capable of a variety of different functions depending on their association with a specific tissue. Myofibroblasts are fibroblasts that express relatively more contractile proteins such as myosin and actin. In situ, fibroblasts reside below the endothelial monolayer that covers the surface of vascular tissue.

The cells can be harvested from the patient's blood or bone marrow. Alternatively, suitable cells could be harvested from, for example, adipose tissue of the patient. The harvesting process can involve liposuction followed by collagenase digestion and purification of microvascular endothelial cells. A suitable process is described further in S. K. Williams, "Endothelial Cell Transplantation," Cell Transplantation 4:401–410 (1995), incorporated herein by reference and in U.S. Pat. Nos. 4,883755, 5,372,945 and 5,628,781, all three incorporated herein by reference.

Purified endothelial cells can be suspended in an appropriate growth media such as M199E (e.g., Sigma Cell Culture, St. Louis, Mo.) with the addition of autologous serum. Other cell types can be suspended similarly. The harvested cells can be contacted with the substrate in a cell culture system to associate the cells with the crosslinked tissue. Thus, a synthetic tissue is formed based on cells from the patient prior to implantation.

Prosthetic tissue can be incubated in a stirred cell suspension for a period of hours to days to allow for cell seeding. Cell seeding provides random attachment of cells that can proliferate to coat the surface of the prosthetic substrate either before or after implantation into the patient. Alternatively, the prosthetic tissue can be incubated under a pressure gradient for a period of minutes to promote cell sodding. A suitable method for cell sodding can be adapted from a procedure described for vascular grafts in the S. K. Williams article, supra. Cell sodding can produce a monolayer of cells on the surface of the prosthetic tissue.

In addition, the prosthetic tissue can be placed in a culture system where the patient's endothelial cells are allowed to migrate onto the surface of the prosthetic substrate from adjacent plastic tissue culture surfaces. If either attachment or migration of endothelial cells is performed under conditions involving physiological shear stress, then the endothelial cells colonizing the surface of the substrate may express appropriate adhesion proteins that allow the cells to adhere more tenaciously following implantation.

Additional Modification of the Crosslinked Tissue

The crosslinked tissue can be further modified to impart desirable properties to the tissue. In particular, the tissue can be treated to stimulate the association of desirable cells with the tissue and/or to reduce calcification of the tissue following implantation. Additional treatment to stimulate association of desirable cells with the tissue can involve affiliation of appropriate compounds, especially proteins, with the cytotoxicity reduced tissue. For example, after the reduction of the cytotoxicity of the tissue with the toxicity reducing agents, the tissue can be associated with one or more growth factors, such as vascular endothelial growth factor (VEGF) and/or fibroblast growth factor, and/or compounds that attract cell precursors to the tissue, attraction compounds.

VEGF refers to a family of polypeptides that have been found to preferentially stimulate growth of vascular endothelial cells over other cells, such as smooth muscle cells. Several forms of VEGF have been identified. VEGF polypeptides generally have sequence homology with platelet-derived growth factor, which can alter the migration and proliferation of a variety of cell types. VEGF has also been referred to as vascular permeability factor. Human recombinant $VEGF_{165}$ is available commercially from R&D Systems, Minneapolis, Minn. The use of VEGF in the production of prostheses has been described further in copending and commonly assigned U.S. patent application Ser. No. 09/014,087 to Carlyle et al., entitled "Prostheses With Associated Growth Factors," and Ser. No. 09/186,810 to Carlyle et al., entitled "Prostheses With Associated Growth Factors," both of which are incorporated herein by reference.

Desirable precursor cells include both progenitor cells that can mature into fibroblasts or endothelial cells, and cells that can differentiate or transdifferentiate into fibroblasts or endothelial cells. Precursor cells circulate in a patients blood steam. These precursor cells are thus available to colonize suitable blood contacting substrates, such as cytotoxicity reduced crosslinked tissue. Suitable precursor cells can be selected from the blood stream and associated with a substrate that serves as the foundation for a viable prosthetic tissue. To initiate the colonization by the precursor cells, an attraction compound can be associated wit the crosslinked tissue. Circulating precursor cells are removed from circulation by the attraction compound and become associated with the cytotoxicity reduced crosslinked tissue The use of attraction compounds to associate precursor cells with a substrate is described further in copending and commonly assigned U.S. patent application Ser. No. 09/203,052, now U.S. Pat. No. 6,375,680 to Carlyle et al., entitled "Substrates For Forming Synthetic Tissue," incorporated herein by reference.

Monocytes and macrophages with a HLA-DR marker on their surfaces are capable of transdifferentiating into fibroblasts. This is described in M. L. Labat et al., "Possible monocytic origin of chondrosarcoma: in vitro transdifferentiation of HLA-DR blood monocyte-like cells from a patient with chondrosarcoma, into neo-fibroblasts and chondrocyte-like cells," Biomed. & Pharmacother 51: 79–93 (1997), incorporated herein by reference. The HLA-DR marker is a protein complex.

In some preferred embodiments of the invention, the HLA-DR marker is used to select for preferred precursor monocytes/macrophages. Monocytes/macrophages with a HLA-DR marker can transdifferentiate spontaneously into fibroblasts, under some circumstances. Antibodies or ligands directed against the HLA-DR marker can serve to bind these monocytes to the cytotoxicity reduced crosslinked tissue.

Precursors for endothelial cells, called angioblasts, are also found in the blood stream. In some preferred embodiments, ligands for the endothelial cell surface marker, endoglin, are used as attraction compounds to select for preferred endothelial cell precursors.

The association of a treatment compound or compounds, e.g., a growth factor and/or an attraction compound, with a cytotoxicity reduced crosslinked tissue each may involve direct attachment, application of a coating including an adhesive or binder, or chemical binding involving a binding agent in addition to the attraction compound/response modifier.

Direct attachment entails combining the substrate with a solution of the treatment compound(s) without the use of an additional chemical binder. With the use of an adhesive, the treatment compound(s) associates with the cytotoxicity reduced crosslinked tissue due to incorporation into the structure of the cured adhesive. Preferred adhesives include, for example, biologic glues such as fibrin glue, and the like. Fibrin glue can be formed from the polymerization of fibrinogen and thrombin. Suitable fibrin glues are available from, for example, Immuno AG, Austria and Zymogenetics, Seattle, Wash.

In other embodiments, the association of a treatment compound(s) with the cytotoxicity reduced crosslinked tissue involves chemical binding initiated by a selected chemical reagent, a chemical binding agent. In contrast to the use of an adhesive, chemical binding involves specific molecular interactions with compositions in the crosslinked tissue, rather than a collective adhesion. Chemical binding can involve covalent bonding, a plurality of noncovalent chemical interactions, or a combination of both covalent and noncovalent interactions. Noncovalent chemical interactions include hydrogen bonding, van der Waals interactions and molecular rearrangements, which characterize specific binding interactions, such as antibody-antigen interactions, protein-receptor binding and enzyme-substrate associations. The chemical binding of the treatment compound(s) with the cytotoxicity reduced crosslinked tissue can involve covalent bonding to the surface of the crosslinked tissue with reactive agents such as glutaraldehyde and other suitable crosslinking agents.

While treatment of the tissue with toxicity reducing agents described herein can also reduce calcification of the tissue following implantation into the patient, it may be desirable to contact the tissue with one or more additional calcification reducing agents. Generally, these additional calcification reducing agents would be contacted with the tissue following crosslinking but before contact with the toxicity reducing agents. Suitable calcification reducing agents include detergents (e.g., sodium dodecyl sulfate), toluidine blue, diphosphonates, and multivalent cations, especially $Al^{+3}$, $Mg^{+2}$ or $Fe^{+3}$ or corresponding metals that can oxidize to form the multivalent metal cations. The effectiveness of $AlCl_3$ and $FeCl_3$ in reducing calcification of crosslinked tissue is described in U.S. Pat. No. 5,368,608 to Levy et al., entitled "Calcification-Resistant Materials and Methods of Making Same Through Use of Multivalent Cations," incorporated herein by reference.

Storage, Distribution and Use

Following treatment with the toxicity reducing agents, the crosslinked tissue, possibly formed into a prosthesis, can be stored. The tissue preferably would not have ingrowth of viable cells if the tissue is intended for longer term storage. Preferred storage techniques minimize the risk of microbial contamination. For example, the crosslinked tissue can be stored in a sealed container with sterile buffer and/or saline solution.

In a sealed container the crosslinked tissue is not subjected to a continuous supply of fluids. Nevertheless, consideration should be given to possible loss during storage of protein modifiers from the tissue or loss during storage of activity of any protein modifiers or the remaining viability of cells associated with the tissue. If excessive loss of tissue constituents is a possibility, the storage time can be limited appropriately to keep the loss to an acceptable level.

For distribution, the crosslinked tissue generally is placed in sealed and sterile containers. Since the tissue has been treated to reduce or eliminate cytotoxicity, care must be taken to ensure acceptable levels of sterility. To ensure maintenance of acceptable levels of sterility, the tissue can be transferred to the sterile container using accepted aseptic protocols. Furthermore, the container with the tissue can be sterilized using radiation before or after sealing the container. The use of electron beam irradiation to sterilize crosslinked tissue is described in U.S. Pat. No. 5,989,498 to Odland, entitled "Electron-Beam Sterilization of Biological Materials," incorporated herein by reference. The containers can be dated such that the date reflects the maximum advisable storage time.

The containers generally are packaged with instructions for the use of the medical devices along with desired and/or required labels. The containers are distributed to health care professionals for surgical implantation of the prostheses. The implantation is performed by a qualified health care professional. The surgical implantation generally involves the replacement of damaged tissue with the prosthesis or the implantation of a catheter or the like to provide suitable access into the patient.

As an alternative to the above storage and distribution approaches, the treatment with toxicity reducing compounds can be performed at a hospital or site remote from the manufacturing site, if desired. This is a particularly suitable approach if the storage time for the cytotoxicity reduced tissue is short. Then, the prosthesis prepared for modification is distributed with a toxicity reducing solution. Alternatively, a toxicity reducing solution is distributed separately from the prosthesis along with instructions for performing crosslinked tissue modification, packaged together as a kit. Then, a selected prosthesis can be modified using the toxicity reducing compositions from the kit prior to implantation. Once the prosthesis is modified with the toxicity reducing agents, it can be implanted, stored for a reasonable period of time or introduced into a cell culture system to affiliate autologous cells with the attractant/response modifier-modified prosthesis.

As noted above, in vitro affiliation of cells with a cytotoxicity reduced crosslinked tissue preferably is performed at hospitals where the patient's cells can be removed for use in a cell culture system. The harvested cells can be contacted with the tissue in a cell culture system to associate the cells with the tissue. Thus, a synthetic tissue is formed based on cells from the patient prior to implantation.

EXAMPLES

Example 1

This example demonstrates the effectiveness of combinations of agents with respect to the reduction of cytotoxicity and of residual aldehyde activity.

A total of 22 solutions were tested in the study. Each solution was contacted with a glutaraldehyde crosslinked porcine aortic heart valve. Porcine valves were procured and crosslinked. To perform the crosslinking, the valves were rinsed with sterile saline and placed into a physiologically buffered 0.5% glutaraldehyde solution. After about 24 hours the solution was refreshed and incubated for at least about 96 hours. The valves were removed from the crosslinking solution and stored in a physiologically buffered 0.5% glutaraldehyde solution for up to 5 years. The valves had dry weights ranging from about 0.47 grams to about 0.51 grams.

To continue processing the valves, the valve jars were placed within a class 100 biological safety cabinet, laminar flow hood. The storage solution was decanted off of the valves and about 60 mls of sterilizing solution was poured into each jar with the valve. The sterilizing solutions contained an aldehyde ethanol solution. The jars with the sterilizing solution were placed in an incubator at a temperature of 30–35° C. for more than 24 hours.

Then, the jars were removed from the incubator and placed back into the laminar flow hood. The sterilizing solution was decanted from the jar, and approximately 60 mls of toxicity reducing solution was added to the jar containing the valve. The toxicity reducing solution was poured off and replaced with another 60 mls of toxicity reducing solution. The formulations of the toxicity reducing solutions are specified in Table 1 below.

TABLE 1

| No. | Amine | EtOH[1] | Sulfate | ($NH_4^+$) | Surf.[2] |
|---|---|---|---|---|---|
| 1 | 2M[3] | | | | |
| 2 | 2M[3] | 90 wt % | | | |
| 3 | 2M[3] | | | | |
| 4 | 2M[3] | | 0.03M SBS[4] 0.04M STS[5] | | |
| 5 | 1M[8] | | 0.03M SBS[4] 0.04M STS[5] | 0.06M ACl[6] | 0.5 wt % |
| 6 | 1M[8] | | 0.03M SBS[4] 0.04M STS[5] | 0.06M ACl[6] | 0.5 wt % |
| 7 | 1M[8] | | 0.03M SBS[4] 0.04M STS[5] | 0.1M ACl[6] 0.1M AOH[7] | 0.5 wt % |
| 8 | 1M[8] | | 0.03M SBS[4] 0.04M STS[5] | 0.1M ACl[6] 0.1M AOH[7] | 0.5 wt % |
| 9 | 1M[8] | | 0.03M SBS[4] 0.04M STS[5] | 0.1M ACl[6] 0.1M AOH[7] | 0.5 wt % |
| 10 | 1M[8] | | 0.03M SBS[4] 0.04M STS[5] | 0.1M ACl[6] 0.1M AOH[7] | 0.5 wt % |
| 11 | 1M[8] | | 0.03M SBS[4] 0.04M STS[5] | 0.1M ACl[6] 0.1M AOH[7] | 0.5 wt % |
| 12 | 1M[8] | | 0.03M SBS[4] 0.04M STS[5] | 0.1M ACl[6] 0.1M AOH[7] | 0.5 wt % |
| 13 | 1M[8] | | 0.03M SBS[4] 0.04M STS[5] | 0.1M ACl[6] 0.1M AOH[7] | 0.5 wt % |
| 14 | 1M[8] | | 0.03M SBS[4] 0.04M STS[5] | 0.1M ACl[6] 0.1M AOH[7] | 0.5 wt % |
| 15 | 1M[8] | | 0.03M SBS[4] 0.04M STS[5] | 0.1M ACl[6] 0.1M AOH[7] | 0.5 wt % |
| 16 | 1M[8] | | 0.03M SBS[4] 0.04M STS[5] | 0.1M ACl[6] 0.1M AOH[7] | 0.5 wt % |
| 17 | 1M[8] | | 0.03M SBS[4] 0.04M STS[5] | 0.1M ACl[6] 0.1M AOH[7] | 0.5 wt % |
| 18 | 1M[8] | | 0.03M SBS[4] 0.04M STS[5] | 0.1M ACl[6] 0.1M AOH[7] | 0.5 wt % |
| 19 | | | | | 0.5 wt % |
| 20 | | | | | 0.5 wt % |
| 21[9] | | | | | |
| 22[9] | | | | | |

[1]EtOH = ethanol
[2]Surf = Tween 80
[3]Amine = glycine-borate
[4]SBS = sodium bisulfate
[5]STS = sodium thiosulfate
[6]ACl = ammonium chloride
[7]AOH = ammonium hydroxide
[8]Amine = glycine
[9]Samples 21 and 22 were sterile water.

The jars with the toxicity reducing solution were placed back into the incubator at 30–35° C. The jars were left in the incubator for varying lengths of time and temperature, as noted in Table 2 below. The valves were removed from the incubators and placed again in laminar flow hoods. The porcine valves were removed from the jars and placed in sterile jars with 300 mls of sterile water. The jars were placed again into the incubator at 30–35° C. for a minimum of three days.

After the jars were removed again from the incubator, 10 ml samples of liquid were removed from the jars for chemical analysis. The chemical analysis was performed to determine the amount of formaldehyde, glutaraldehyde and ethanol that were extracted into the liquid. The aldehydes were evaluated using high-performance liquid chromatography (HPLC). The ethanol concentrations were evaluated by gas chromatography.

To measure the aldehyde concentrations, a one ml aliquot of each sample was diluted by a factor of 1000 with reverse osmosis purified water with a residual electrical resistance of greater than about 16 megaohms. A 1.35 ml quantity of 0.01 M 2,4-dinitrophenol hydrazine solution was added to derivatize the aldehydes. The samples were then injected onto a Waters™ 2690 HPLC separation module connected to a 2487 PDA detector. A gradient profile was generated in which a mixture of 50% by weight water and 50% by weight acetonitrile changed over to 100% pure acetonitrile over a twenty minute period. One hundred percent pure acetonitrile was run through the column for two minutes. Then, a second gradient was run through the column going from 100% pure acetonitrile to a mixture of 50% by weight water and 50% by weight acetonitrile over a three minute period. Total run time was 25 minutes.

Formaldehyde and glutaraldehyde were distinguished based on their elution times from the column such that the elution times corresponded to the elution times of standards run on the HPLC. The values of the aldehyde concentrations were evaluated by generating a standard curve from standard samples with concentrations from 3 ppm to 50 ppm. The sample values were determined by interpolation or extrapolation on the standard curve. The values are given in Table 2.

The amount of ethanol was evaluated using a Perkin-Elmer™ Gas Chromatograph. A Perkin-Elmer™ autosystem with a 0.25 mm fused silica capillary column and turbochrome software was used. The dilution factor was 500. The temperature gradient was 40 to 260 degrees C. in 23 minutes. The detection and quantification limits were 20 ppm. These results are also presented in Table 2.

TABLE 2

| No. | Incubation Time | Incubation Temp. | Form[1] | Glut.[2] | EtOH[3] |
|---|---|---|---|---|---|
| 1 | 10 min. | Room Temp. | 58 ppm | BQL[4] | 1400 ppm |
| 2 | 10 min. | Room Temp. | 100 ppm | 100 ppm | 4800 ppm |
| 3 | 4 hrs. | 37 ± 2° C. | 14.5 ppm | BQL | 485 ppm |
| 4 | 2 min. | Room Temp. | 151.9 ppm | BQL | 1800 ppm |
| 5 | 6 min. | Room Temp. | 150 ppm | BQL | 1582 ppm |
| 6 | 4 hrs. | 37 ± 2° C. | 9.8 ppm | BQL | 206 ppm |
| 7 | 4 hrs. | 37 ± 2° C. | 9.4 ppm | BQL | 164 ppm |
| 8 | 24 hrs. | 37 ± 2° C. | 7.3 ppm | BQL | 186 ppm |
| 9 | 1 hr. | Room Temp. | 39.9 ppm | BQL | 673 ppm |
| 10 | 2 hrs. | Room Temp. | 19.74 ppm | BQL | 281 ppm |
| 11 | 4 hrs. | 30–35° C. | 8.56 ppm | BQL | 160 ppm |
| 12 | 24 hrs. | 30–35° C. | 5.33 ppm | BQL | 170 ppm |
| 13 | 4 hrs. | 30–35° C. | 10.48 ppm | BQL | 184 ppm |
| 14 | 24 hrs. | 30–35° C. | 5.20 ppm | BQL | 179 ppm |
| 15 | 4 hrs. | 30–35° C. | 5.1 ppm | BQL | 161 ppm |
| 16 | 24 hrs. | 30–35° C. | 8.2 ppm | BQL | 174 ppm |
| 17 | 4 hrs. | 30–35° C. | 9.75 ppm | BQL | 186 ppm |
| 18 | 4 hrs. | 30–35° C. | 14.28 ppm | BQL | 275 ppm |
| 19 | 4 hrs. | 30–35° C. | 65.42 ppm | 43.1 ppm | 412 ppm |
| 20 | 4 hrs. | 30–35° C. | 42.1 ppm | 26.2 ppm | 233 ppm |
| 21 | 4 hrs. | 30–35° C. | 53 ppm | 33.64 ppm | 327 ppm |
| 22 | 4 hrs. | 30–35° C. | 64.18 ppm | 45.52 ppm | 400 ppm |

[1]Form. = formaldehyde
[2]Glut. = glutaraldehyde
[3]EtOH = ethanol
[4]BQL = Below Quantifiable Limit (<3 ppm)

Following the last incubation, the cytotoxicity of the valves to microorganisms was tested. The cytotoxicity of the cytotoxicity reduced crosslinked tissue was evaluated under procedures outlined for Validation Tests in the U.S. Pharmacopeia, Eighth Supplement, Chapter 71 (1998), incorporated herein by reference, relating to Sterility Tests. The results for samples 1–16 and 21–22 are summarized in Table 3.

TABLE 3

| No. | Sterility Test Results |
|---|---|
| 1 | Growth of CS and SA. No growth of BS and CA. |
| 2 | Growth of CS and SA. No growth of BS and slow growth of CA. |
| 3 | Growth of CS and SA. Slow growth of BS and CA. |
| 4 | Growth of CS, SA and CA. No growth of BS. |
| 5 | Growth of CS. Slow growth of CA and SA. No growth of BS. |
| 6 | All growth equivalent. |
| 7 | All growth equivalent. |
| 8 | All growth equivalent. |
| 9 | All growth equivalent. |
| 10 | All growth equivalent. |
| 11 | All growth equivalent. |
| 12 | All growth equivalent. |
| 13 | All growth equivalent. |
| 14 | All growth equivalent. |
| 15 | All growth equivalent. |
| 16 | All growth equivalent. |
| 21 | No growth. |
| 22 | No growth. |

CS = *Clostridium sporogenes* — 3 day incubation
SA = *Staphylococcus aureus* — 3 day incubation
BS = *Bacillus subtilis* — 3 day incubation
CA = *Candida albicans* — 5 day incubation Based on the results presented in Tables 2 and 3, it follows that excellent cytotoxicity reduction is obtained with the formulation of toxicity reducing agents corresponding to samples 11–18 with incubations from 4 hours to 24 hours at temperatures from 30–35° C.

Example 2

Four additional samples were prepared to evaluate association of endothelial cells with crosslinked tissue. Two samples were prepared from a glutaraldehyde crosslinked porcine heart valve treated with toxicity reducing solution No. 7 for 4 hours. No growth factors or other compounds were added. Sample 1 was a leaflet portion of the valve and sample 2 was a root portion of the valve. A third sample was a leaflet portion treated with 90% ethanol for 24 hours, and a fourth sample was a leaflet portion not treated to reduce cytotoxicity. All four samples were pre-incubated in serum-free media for 30 minutes.

Human aortic endothelial cells (HAECs) from Clonetics, Inc. (San Diego, Calif., lot HAEC 2508) were grown and harvested using standard cell culture techniques. The cells were stained with the viable fluorescent dye, dioctadecyl tetramethyl indocarbocyanine perchlorate (DiI) from Molecular Probes Inc., Eugene, Oreg. (catalog No. D-282), for fifteen minutes and then rinsed to remove extraneous dye. The stained HAECs were suspended in serum-free medium at a concentration of $5 \times 10^5$ cells/ml.

Two mls of stained cell suspension were pipetted onto each sample. Then, the inoculated samples were incubated for 2.5 hours at 37° C. with 5% $CO_2$. After incubation, the leaflets were rinsed three times with saline and fixed with 3% phosphate buffered formaldehyde. The tissue samples were examined with a Nikon® Ellipse 600 microscope with an epi-fluorescent attachment. There was significant cell attachment and spreading on both of the first two samples. The third sample also had significant cell attachment. Sample 4, the glutaraldehyde crosslinked sample with no cytotoxicity reduction treatment, had few cells attached and no spreading.

The embodiments described above are intended to be exemplary and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. A prosthetic tissue comprising a chemically crosslinked protein matrix comprising aldehyde adducts, the protein matrix having immunological rejection sufficiently suppressed to permit xenograft transplantation and the protein matrix having no detectable cytotoxicity as evaluated in a culture medium without any added growth factors.

2. The prosthetic tissue of claim 1 comprising adducts of aldehyde functional groups and sulfur-oxygen compounds.

3. The prosthetic tissue of claim 1 comprising adducts of aldehyde functional groups and amines.

4. The prosthetic tissue of claim 1 comprising adducts of aldehyde functional groups and ammonia/ammonium.

5. The prosthetic tissue of claim 1 comprising adducts of aldehyde functional groups and amino acids.

6. The prosthetic tissue of claim 1 further comprising a growth factor.

7. The prosthetic tissue of claim 6 wherein the growth factor is vascular endothelial growth factor.

8. The prosthetic tissue of claim 1 further comprising compounds that attract cell precursors.

9. A heart valve prosthesis comprising the prosthetic tissue of claim 1.

10. A vascular graft comprising the prosthetic tissue of claim 1.

11. A prosthetic tissue comprising a protein matrix crosslinked with a multifunctional aldehyde and soaked in formaldehyde having extractable residual aldehyde compound concentrations of no more than about $5 \times 10^{-4}$ moles of aldehyde per gram of dry tissue.

12. The prosthetic tissue of claim 11 wherein residual aldehyde concentration is no more than about $2 \times 10^{-4}$ moles of aldehyde per gram of dry tissue.

13. The prosthetic tissue of claim 11 having a residual multifunctional aldehyde concentration no more than about $6 \times 10^{-5}$ moles of multifunctional aldehyde per gram of dry tissue.

14. The prosthetic tissue of claim 11 having a residual multifunctional aldehyde concentration no more than about $1 \times 10^{-5}$ moles of multifunctional aldehyde per gram of dry tissue.

15. The prosthetic tissue of claim 11 having a residual formaldehyde concentration no more than about $1 \times 10^{-4}$ moles of formaldehyde per gram of dry tissue.

16. The prosthetic tissue of claim 11 having a residual formaldehyde concentration no more than about $2 \times 10^{-5}$ moles of formaldehyde per gram of dry tissue.

17. The prosthetic tissue of claim 11 having no detectable cytotoxicity without any added growth hormones.

18. A prosthetic tissue comprising adducts of aldehyde groups and inorganic sulfur-oxygen groups.

19. The prosthetic tissue of claim 18 further comprising adducts of aldehyde groups and amines.

20. The prosthetic tissue of claim 19 wherein the amine comprises glycine.

21. The prosthetic tissue of claim 18 further comprising adducts of aldehyde groups and ammonia/ammonium.

22. The prosthetic tissue of claim 18 further comprising a surfactant.

23. The prosthetic tissue of claim 18 wherein the inorganic sulfur-oxygen compound comprises a bisulfate compound.

24. The prosthetic tissue of claim 18 wherein the inorganic sulfur-oxygen compound comprises a thiosulfate compound.

25. The prosthetic tissue of claim 18 further comprising an adduct of organic sulfates and aldehyde groups.

26. The prosthetic tissue of claim 18 further comprising a growth factor.

27. The prosthetic tissue of claim 26 wherein the growth factor is vascular endothelial growth factor.

28. The prosthetic tissue of claim 18 further comprising compounds that attract cell precursors.

29. The prosthetic tissue of claim 18 further comprising adducts of aldehyde groups and an amino acid, adducts of aldehyde groups and ammonia/ammonium, and a surfactant.

30. A heart valve prosthesis comprising prosthetic tissue of claim 18.

31. A vascular graft comprising prosthetic tissue of claim 18.

32. A prosthetic tissue comprising adducts of aldehyde groups and ammonia/ammonium groups and adducts of aldehyde groups and sulfur-oxygen groups.

33. The prosthetic tissue of claim 32 wherein the sulfur-oxygen groups comprises organic sulfate groups.

* * * * *